US011517708B2

(12) United States Patent
Espi Maques et al.

(10) Patent No.: US 11,517,708 B2
(45) Date of Patent: *Dec. 6, 2022

(54) EAR-WORN ELECTRONIC DEVICE FOR CONDUCTING AND MONITORING MENTAL EXERCISES

(71) Applicant: Starkey Laboratories, Inc., Eden Prairie, MN (US)

(72) Inventors: Miquel Espi Maques, Berkeley, CA (US); Sahar Akram, Berkeley, CA (US); Navin Chatlani, Berkeley, CA (US); Karim Helwani, Eden Prairie, MN (US); Carlos Renato Nakagawa, Eden Prairie, MN (US); Tao Zhang, Eden Prairie, MN (US)

(73) Assignee: Starkey Laboratories, Inc., Eden Prairie, MN (US)

(*) Notice: Subject to any disclaimer, the term of this patent is extended or adjusted under 35 U.S.C. 154(b) by 350 days.

This patent is subject to a terminal disclaimer.

(21) Appl. No.: 16/831,189

(22) Filed: Mar. 26, 2020

(65) Prior Publication Data
US 2020/0230347 A1 Jul. 23, 2020

Related U.S. Application Data

(63) Continuation of application No. 15/664,127, filed on Jul. 31, 2017, now Pat. No. 10,617,842.

(51) Int. Cl.
*A61M 21/02* (2006.01)
*G09B 19/00* (2006.01)
(Continued)

(52) U.S. Cl.
CPC ............ *A61M 21/02* (2013.01); *A61B 5/165* (2013.01); *A61B 5/369* (2021.01); *A61B 5/6815* (2013.01);
(Continued)

(58) Field of Classification Search
CPC ........ A61M 21/02; A61B 5/165; A61B 5/369; A61B 5/6815
See application file for complete search history.

(56) References Cited

U.S. PATENT DOCUMENTS

| 6,118,875 | A | 9/2000 | Moeller et al. |
| 6,305,943 | B1 | 10/2001 | Pougatchev et al. |
(Continued)

FOREIGN PATENT DOCUMENTS

| DE | 102011107247 | 9/2001 |
| EP | 1646265 | 2/2010 |
(Continued)

OTHER PUBLICATIONS

Non Final Office Action dated Mar. 10, 2022 for U.S. Appl. No. 16/027,903, filed Jul. 5, 2018, Inventor: Christine Marie Tan.
(Continued)

*Primary Examiner* — John P Lacyk
(74) *Attorney, Agent, or Firm* — Mueting Raasch Group

(57) ABSTRACT

An ear-worn electronic device includes a right ear device comprising a first processor and a left ear device comprising a second processor communicatively coupled to the first processor. A physiologic sensor module comprises one or more physiologic sensors configured to sense at least one physiologic parameter from a wearer. A motion sensor module comprises one or more sensors configured to sense movement of the wearer. The first and second processors are coupled to the physiologic and motion sensor modules. The first and second processors are configured to produce a three-dimensional virtual sound environment comprising relaxing sounds, generate verbal instructions within the three-dimensional virtual sound environment that guide the wearer through a predetermined mental exercise that promotes wearer relaxation, and generate verbal commentary that assesses wearer compliance with the predetermined (Continued)

mental exercise in response to one or both of the sensed movement and the at least one physiologic parameter.

25 Claims, 9 Drawing Sheets

(51) Int. Cl.
| | |
|---|---|
| A61B 5/16 | (2006.01) |
| G09B 5/04 | (2006.01) |
| A61B 5/00 | (2006.01) |
| H04R 5/033 | (2006.01) |
| G10K 11/178 | (2006.01) |
| G16H 20/70 | (2018.01) |
| A61B 5/369 | (2021.01) |
| A61M 21/00 | (2006.01) |
| H04S 7/00 | (2006.01) |
| G10K 11/175 | (2006.01) |
| H04R 1/10 | (2006.01) |

(52) U.S. Cl.
CPC .............. *G09B 5/04* (2013.01); *G09B 19/00* (2013.01); *G10K 11/17823* (2018.01); *G10K 11/17837* (2018.01); *G10K 11/17873* (2018.01); *G16H 20/70* (2018.01); *H04R 5/033* (2013.01); *A61B 5/4803* (2013.01); *A61B 5/4833* (2013.01); *A61B 5/4848* (2013.01); *A61M 2021/0027* (2013.01); *A61M 2205/3303* (2013.01); *A61M 2205/3375* (2013.01); *A61M 2205/3569* (2013.01); *A61M 2205/3592* (2013.01); *A61M 2205/50* (2013.01); *A61M 2209/088* (2013.01); *A61M 2210/0662* (2013.01); *A61M 2230/06* (2013.01); *A61M 2230/10* (2013.01); *A61M 2230/18* (2013.01); *A61M 2230/205* (2013.01); *A61M 2230/30* (2013.01); *A61M 2230/40* (2013.01); *A61M 2230/42* (2013.01); *A61M 2230/50* (2013.01); *A61M 2230/63* (2013.01); *A61M 2230/65* (2013.01); *G10K 11/175* (2013.01); *G10K 2210/30231* (2013.01); *H04R 1/1083* (2013.01); *H04R 2460/07* (2013.01); *H04S 7/304* (2013.01); *H04S 2420/01* (2013.01)

(56) References Cited

U.S. PATENT DOCUMENTS

| | | | |
|---|---|---|---|
| 6,955,542 B2 | 10/2005 | Roncalez et al. | |
| 7,252,640 B2 | 8/2007 | Ni et al. | |
| 7,267,652 B2 | 9/2007 | Coyle et al. | |
| 7,510,531 B2 | 3/2009 | Lee et al. | |
| 8,500,635 B2 | 8/2013 | Zilca et al. | |
| D709,673 S | 7/2014 | Aimone et al. | |
| 8,888,700 B2 | 11/2014 | Banet et al. | |
| 8,972,197 B2 | 3/2015 | Jangle et al. | |
| 9,744,330 B2 | 8/2017 | Searchfield et al. | |
| 9,779,751 B2 | 10/2017 | Bikko | |
| 9,820,911 B2 | 11/2017 | Shoshani | |
| 9,830,832 B2 | 11/2017 | Warren et al. | |
| 9,924,271 B2 | 3/2018 | Lai et al. | |
| 9,933,989 B2 | 4/2018 | Tsingos et al. | |
| 9,983,670 B2 | 5/2018 | Coleman et al. | |
| 9,999,280 B2 | 6/2018 | Zebley | |
| 10,120,413 B2 | 11/2018 | Aimone et al. | |
| 10,178,487 B2 | 1/2019 | Anastas | |
| 10,188,345 B2 | 1/2019 | Venkatraman et al. | |
| 10,219,740 B2 | 3/2019 | Warren et al. | |
| 10,365,716 B2 | 7/2019 | Aimone et al. | |
| 10,582,908 B2 | 3/2020 | Stroman | |
| 10,617,842 B2 | 4/2020 | Espi Maques et al. | |
| 2004/0225340 A1 | 11/2004 | Evans | |
| 2008/0015457 A1 | 1/2008 | Silva | |
| 2009/0263773 A1 | 10/2009 | Kotlyar et al. | |
| 2013/0053718 A1 | 2/2013 | Hung et al. | |
| 2013/0061178 A1 | 3/2013 | Selig | |
| 2013/0343584 A1 | 12/2013 | Bennett et al. | |
| 2014/0356823 A1 | 12/2014 | Theeuwes | |
| 2015/0351655 A1 | 12/2015 | Coleman | |
| 2017/0172459 A1 | 6/2017 | Bernstein | |
| 2017/0258329 A1 | 9/2017 | Marsh | |
| 2018/0014741 A1 | 1/2018 | Chou | |
| 2018/0020937 A1 | 1/2018 | Chou | |
| 2018/0122509 A1 | 5/2018 | Christiansson | |
| 2018/0296877 A1 | 10/2018 | Reeh et al. | |
| 2018/0310855 A1 | 11/2018 | Connor | |
| 2019/0029563 A1 | 1/2019 | Sels et al. | |
| 2019/0038179 A1 | 2/2019 | Tanriover et al. | |

FOREIGN PATENT DOCUMENTS

| | | |
|---|---|---|
| EP | 3154278 | 4/2017 |
| WO | 2014/010165 | 1/2014 |

OTHER PUBLICATIONS

Motions, Biometric Research Platform, "EEG Pocket Guide", 2016, 72 pages.
Zhang et al., "Surround by Sound: A Review of Spatial Audio Recording and Reproduction", Applied Sciences, No. 7, May 20, 2017, 19 pages.
Abushakra and Faezipour, "Acoustic Signal Classification of Breathing Movements to Virtually Aid Breath Regulation," IEEE Journal of Biomedical and Health Informatics, Mar. 2013, 17(2):1493-500.
EP Search Report for 19184804.3 dated Oct. 9, 2019, 17 pages.
Hartmann, Signals, Sound, and Sensation. American Institute of Physics, Woodbury, N.Y, 1997. Cover Page, Summary, and Table of Contents. 3 pages.
Jarne, "Simple empirical algorithm to obtain signal envelope in three steps," Mar. 20, 2017, published online by arXiv. Cited as: arXiv:1703.06812v1. Available on the internet URL:https://ia801506.us.archive.org/1/items/arxiv-1703.06812/1703.06812.pdf; 10 pages.
Office Action from EP Application No. 19184804.3 dated Mar. 4, 2020, 17 pages.
Potamianos and Maragos, "A Comparison of the Energy Operator and the Hilbert Transform Approach to Signal and Speech Demodulation," Signal Processing, May 1994; 37(1):95-120.
Schloss, "On the Automatic Transcription of Percussive Music— From Acoustic Signal to High-Level Analysis," Thesis, 1985, Stanford University; 126 pages.
Yahya and Faezipour, "Automatic Detection and Classification of Acoustic Breathing Cycles," Presented at the 2014 Zone 1 Conference of the American Society for Engineering Education, Apr. 3-5, 2014, Bridgeport, Connecticut, USA. Published in Proceedings of the 2014 Zone 1 Conference of the American Society for Engineering Education, May 2014; 6 pages.
Office Action from U.S. Appl. No. 16/027,903 dated Jan. 4, 2021, 22 pages.

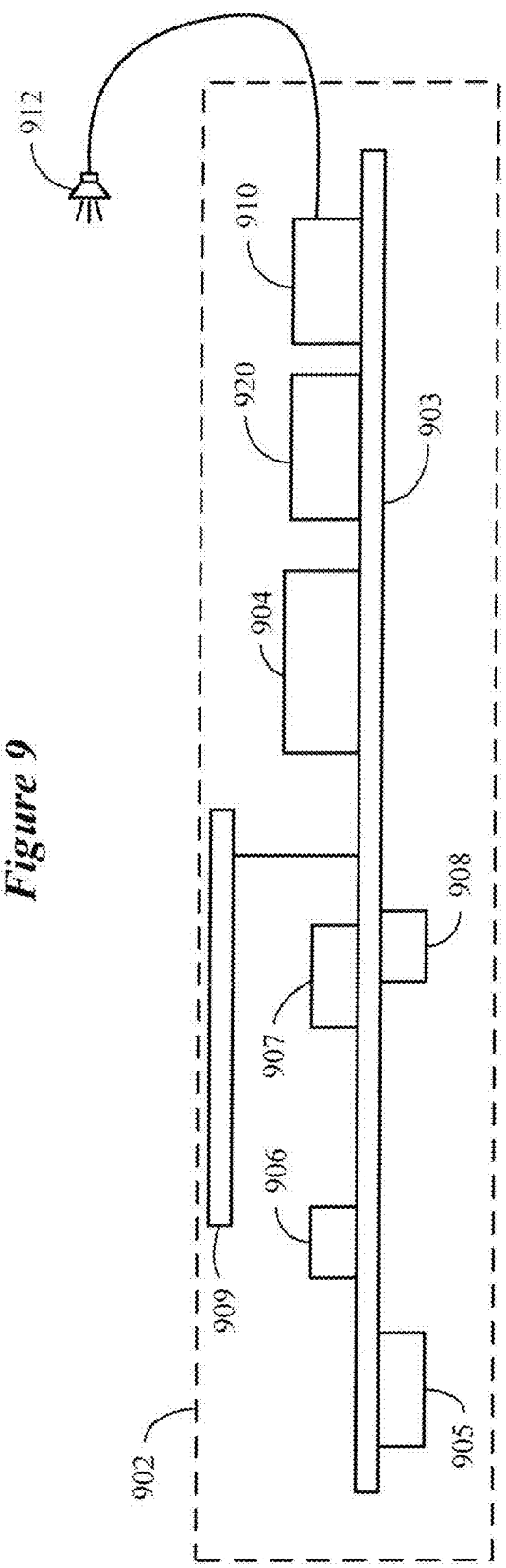

EAR-WORN ELECTRONIC DEVICE FOR CONDUCTING AND MONITORING MENTAL EXERCISES

RELATED PATENT DOCUMENTS

This application is a continuation of U.S. patent application Ser. No. 15/664,127, filed Jul. 31, 2017, which is incorporated herein by reference in its entirety.

TECHNICAL FIELD

This application relates generally to hearing devices, including ear-worn electronic devices, hearing aids, personal amplification devices, and other hearables.

BACKGROUND

Mental exercises, such as meditation, are difficult to perform by persons given their busy working schedules and lack of convenient spaces. When performing a mental exercise in a place not originally designed for that purpose, there are often plenty of potentially distracting events and important events that can interfere with the proper execution of the mental exercise. Generally, a trained instructor is needed to successfully guide persons through a mental exercise. Access to such trained instructors involves expense and inconvenience of having to travel to meet personally with an instructor. Typically, trained instructors only make use of external factors (subjective measures) to evaluate a person's performance during a session involving mental exercises over time and provide recommendations without access to mental and physiological factors (objective measures). Even when these factors are accessed, such access requires the use of equipment that is distracting and intrusive to the mental exercise.

SUMMARY

Various embodiments are directed to method implemented by an ear-worn electronic device configured to be worn by a wearer and comprising a right ear device and a left ear device. The method comprises producing, by the ear-worn electronic device, a three-dimensional virtual sound environment comprising relaxing sounds. The method comprises generating, by the ear-worn electronic device, verbal instructions within the three-dimensional virtual sound environment that guide the wearer through a predetermined mental exercise that promotes wearer relaxation. The method comprises sensing, during the predetermined mental exercise, at least one physiologic parameter from the wearer by the ear-worn electronic device. The method also comprises sensing, during the predetermined mental exercise, movement of the wearer by the ear-worn electronic device. The method further comprises generating, by the ear-worn electronic device, verbal commentary that assesses wearer compliance with the predetermined mental exercise in response to one or both of the at least one physiologic parameter and the sensed movement of the wearer.

According to other embodiments, an ear-worn electronic device is configured to be worn by a wearer and comprises a right ear device comprising a first processor and a left ear device comprising a second processor communicatively coupled to the first processor. A physiologic sensor module comprises one or more physiologic sensors configured to sense at least one physiologic parameter from the wearer. A motion sensor module comprises one or more sensors configured to sense movement of the wearer. The first and second processors are coupled to the physiologic and motion sensor modules. The first and second processors are configured to produce a three-dimensional virtual sound environment comprising relaxing sounds, generate verbal instructions within the three-dimensional virtual sound environment that guide the wearer through a predetermined mental exercise that promotes wearer relaxation, and generate verbal commentary that assesses wearer compliance with the predetermined mental exercise in response to one or both of the sensed movement and the at least one physiologic parameter.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings wherein:

FIG. 9 is a block diagram showing various components of an ear-worn electronic device that can be configured to conduct and monitor a mental exercise performed by a wearer of the device in accordance with various embodiments.

The figures are not necessarily to scale. Like numbers used in the figures refer to like components. However, it will be understood that the use of a number to refer to a component in a given figure is not intended to limit the component in another figure labeled with the same number;

DETAILED DESCRIPTION

Figure 1:
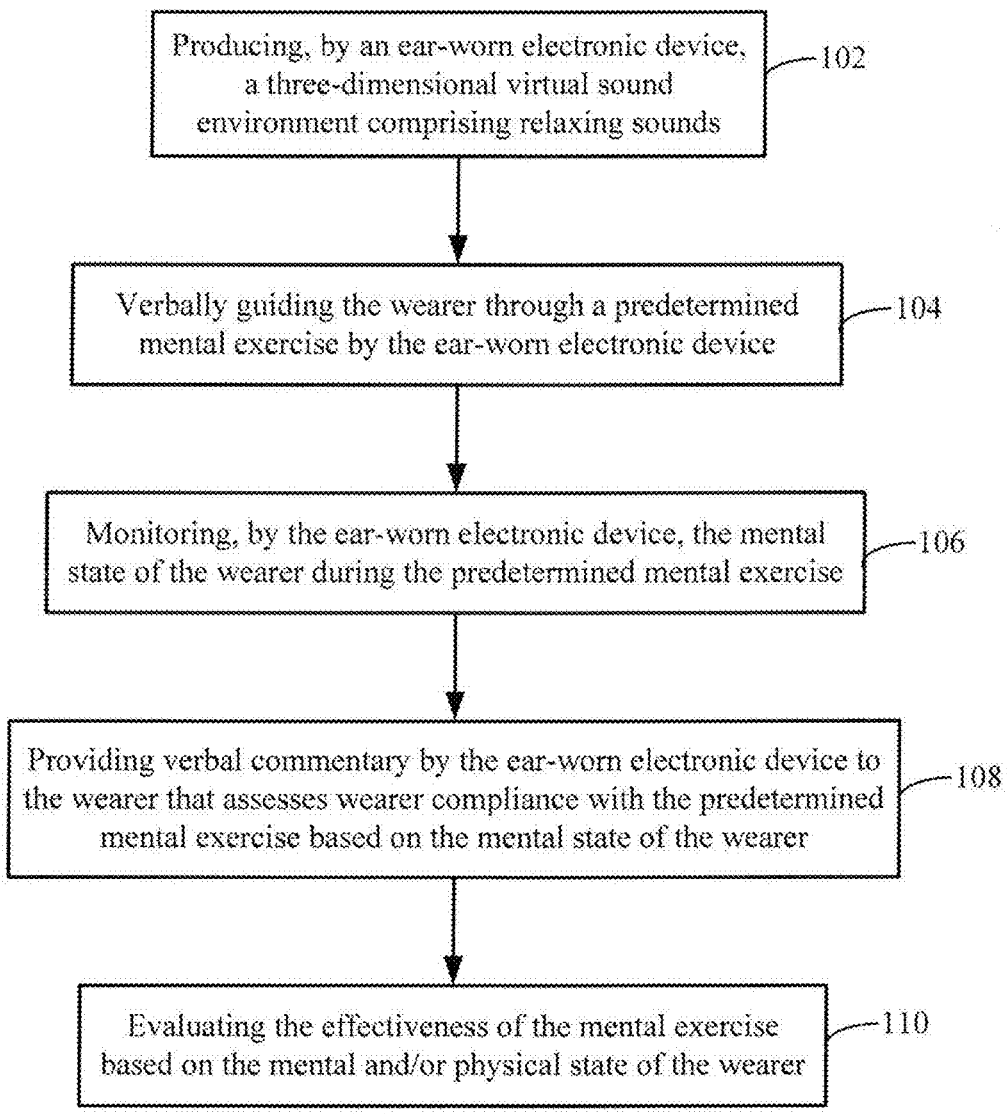
FIG. 1 illustrates various processes of a method implemented by an ear-worn electronic device in accordance with various embodiments.

It is understood that the embodiments described herein may be used with any ear-worn electronic device without departing from the scope of this disclosure. The devices depicted in the figures are intended to demonstrate the subject matter, but not in a limited, exhaustive, or exclusive sense. Ear-worn electronic devices, such as hearables (e.g., wearable earphones and earbuds), hearing aids, and hearing assistance devices, typically include an enclosure, such as a housing or shell, within which internal components are disposed. Typical components of an ear-worn electronic device can include a digital signal processor (DSP), memory, power management circuitry, one or more communication devices (e.g., a radio, a near-field magnetic induction (NFMI) device), one or more antennas, one or more microphones, and a receiver/speaker, for example. Some ear-worn electronic devices can incorporate a long-range communication device, such as a Bluetooth® transceiver or other type of radio frequency (RF) transceiver. A communication device (e.g., a radio or NFMI device) of an ear-worn electronic device can be configured to facilitate communication between a left ear device and a right ear device of the ear-worn electronic device.

Ear-worn electronic devices of the present disclosure can incorporate an antenna arrangement coupled to a high-frequency radio, such as a 2.4 GHz radio. The radio can conform to an IEEE 802.11 (e.g., WiFi®) or Bluetooth® (e.g., BLE, Bluetooth® 4. 2 or 5.0) specification, for example. It is understood that hearing devices of the present disclosure can employ other radios, such as a 900 MHz radio. Ear-worn electronic devices of the present disclosure can be configured to receive streaming audio (e.g., digital audio data or files) from an electronic or digital source. Representative electronic/digital sources (e.g., accessory devices) include an assistive listening system, a TV streamer, a radio, a smartphone, a laptop, a cell phone/entertainment device (CPED) or other electronic device that serves as a source of digital audio data or other types of data files. Ear-worn electronic devices of the present disclosure can be configured to effect bi-directional communication (e.g., wireless communication) of data with an external source, such as a remote server via the Internet or other communication infrastructure.

The term ear-worn electronic device of the present disclosure refers to a wide variety of ear-level electronic devices that can aid a person with impaired hearing. The term ear-worn electronic device also refers to a wide variety of devices that can produce optimized or processed sound for persons with normal hearing. Ear-worn electronic devices of the present disclosure include hearables (e.g., wearable earphones, headphones, earbuds, virtual reality headsets), hearing aids (e.g., hearing instruments), and cochlear implants, for example. Ear-worn electronic devices include, but are not limited to, behind-the-ear (BTE), in-the-ear (ITE), in-the-canal (ITC), invisible-in-canal (IIC), receiver-in-canal (RIC), receiver-in-the-ear (RITE) or completely-in-the-canal (CIC) type hearing devices or some combination of the above. Throughout this disclosure, reference is made to an "ear-worn electronic device," which is understood to refer to a system comprising a left ear device and a right ear device.

Embodiments of the disclosure are directed to an ear-worn electronic device configured to conduct and monitor a mental exercise performed by a wearer of the device. For example, an ear-worn electronic device can be configured to guide a wearer through various exercises that focus on the human mind, such as meditation, mindfulness, hypnosis, yoga, Qi Gong, and Tai Chi. Embodiments are directed to an ear-worn electronic device that provides an immersive and relaxing sound environment for a wearer while performing a mental exercise. Verbal instructions are provided by the ear-worn electronic device to guide the wearer through the mental exercise, and the mental and/or physical state of the wearer is evaluated by the ear-worn electronic device during the exercise. In response to the mental and/or physical state of the wearer, positive and corrective verbal feedback is provided by the ear-worn electronic device to encourage wearer compliance with the mental exercise. The ear-worn electronic device can also monitor the sound environment and provide guidance to the wearer to either ignore or pay attention to external events. A user profile can be developed over time for the wearer based on data indicating which soundscapes, exercises, and instructions help the specific wearer achieve optimal performance.

FIG. 1 illustrates various processes of a method implemented by an ear-worn electronic device in accordance with various embodiments. The method of FIG. 1 involves producing 102, by an ear-worn electronic device, a three-dimensional (3-D) virtual sound environment comprising relaxing sounds. The relaxing sounds may comprise music (e.g., slow tempo instrumental music), nature sounds (rain, thunder, running water, ocean sounds, wind, and bird calls), and/or other sounds that promote relaxation. The method involves verbally guiding 104 the wearer through a predetermined mental exercise by the ear-worn electronic device. The method also involves monitoring 106, by the ear-worn electronic device, the mental state of the wearer during the predetermined mental exercise. The method further involves providing 108 verbal commentary by the ear-worn electronic device to the wearer that assesses wearer compliance with the predetermined mental exercise based on the mental state of the wearer.

Figure 2:
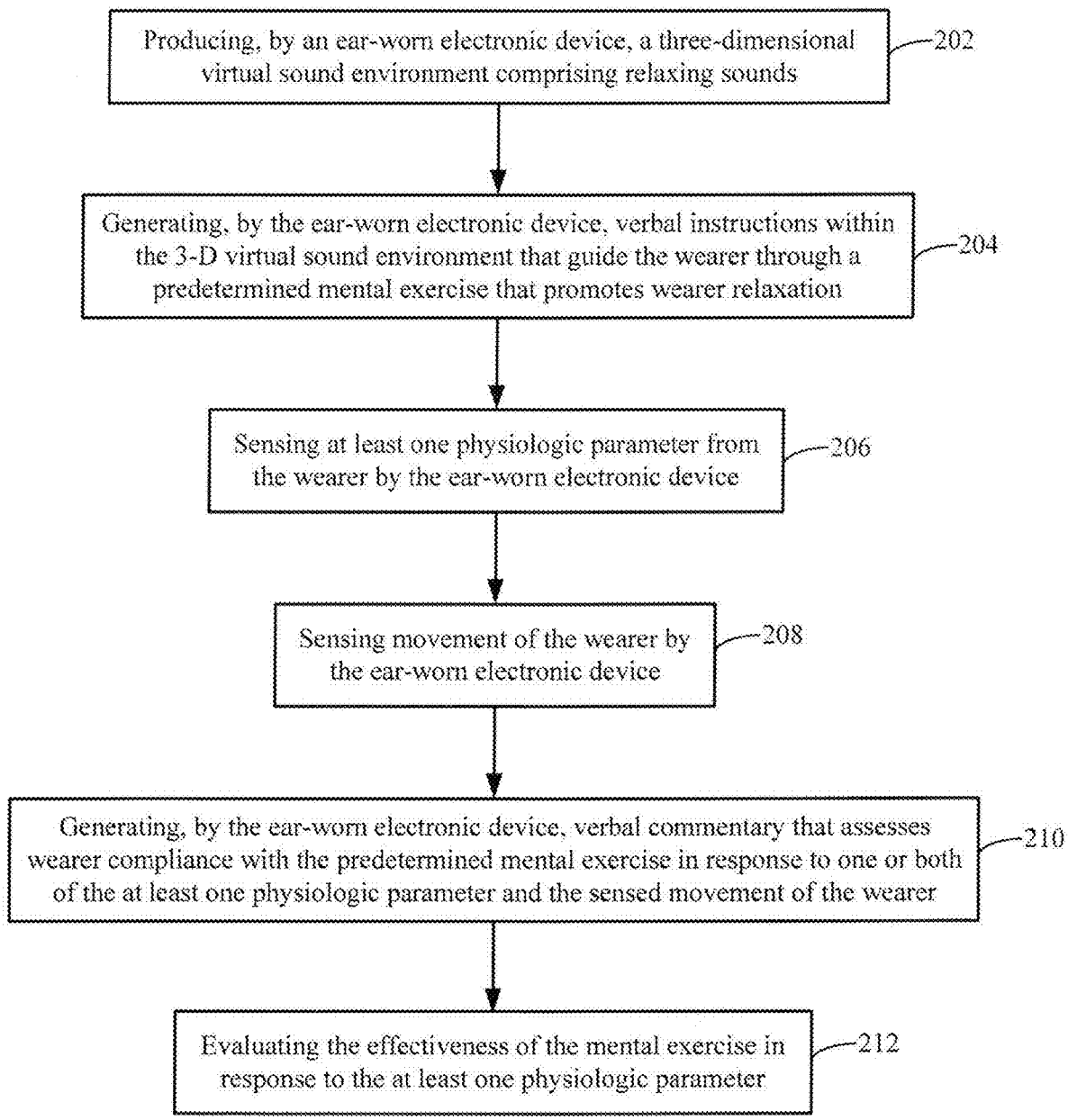
FIG. 2 illustrates various processes of a method implemented by an ear-worn electronic device in accordance with various embodiments.

FIG. 2 illustrates various processes of a method implemented by an ear-worn electronic device in accordance with various embodiments. The method of FIG. 2 involves producing 202, by an ear-worn electronic device, a 3-D virtual sound environment comprising relaxing sounds. The method involves generating 204, by the ear-worn electronic device, verbal instructions within the 3-D sound environment that guide the wearer through a predetermined mental exercise that promotes wearer relaxation. The method involves sensing 206 at least one physiologic parameter from the wearer by the ear-worn electronic device. The method also involves sensing 208 movement of the wearer by the ear-worn electronic device during the mental exercise. The method further involves generating 210, by the ear-worn electronic device, verbal commentary that assesses wearer compliance with the predetermined mental exercise in response to one or both of the at least one physiologic parameter and the sensed movement of the wearer. In some embodiments, the verbal commentary that assesses wearer compliance with the predetermined mental exercise is based solely on one or more physiologic parameters sensed by the ear-worn electronic device. In other embodiments, the verbal commentary is based solely on the sensed movement of the wearer by the year-worn electronic device. In further embodiments, the verbal commentary is based on both the sensed movement and one or more physiologic parameters sensed by the ear-worn electronic device.

Figure 3:
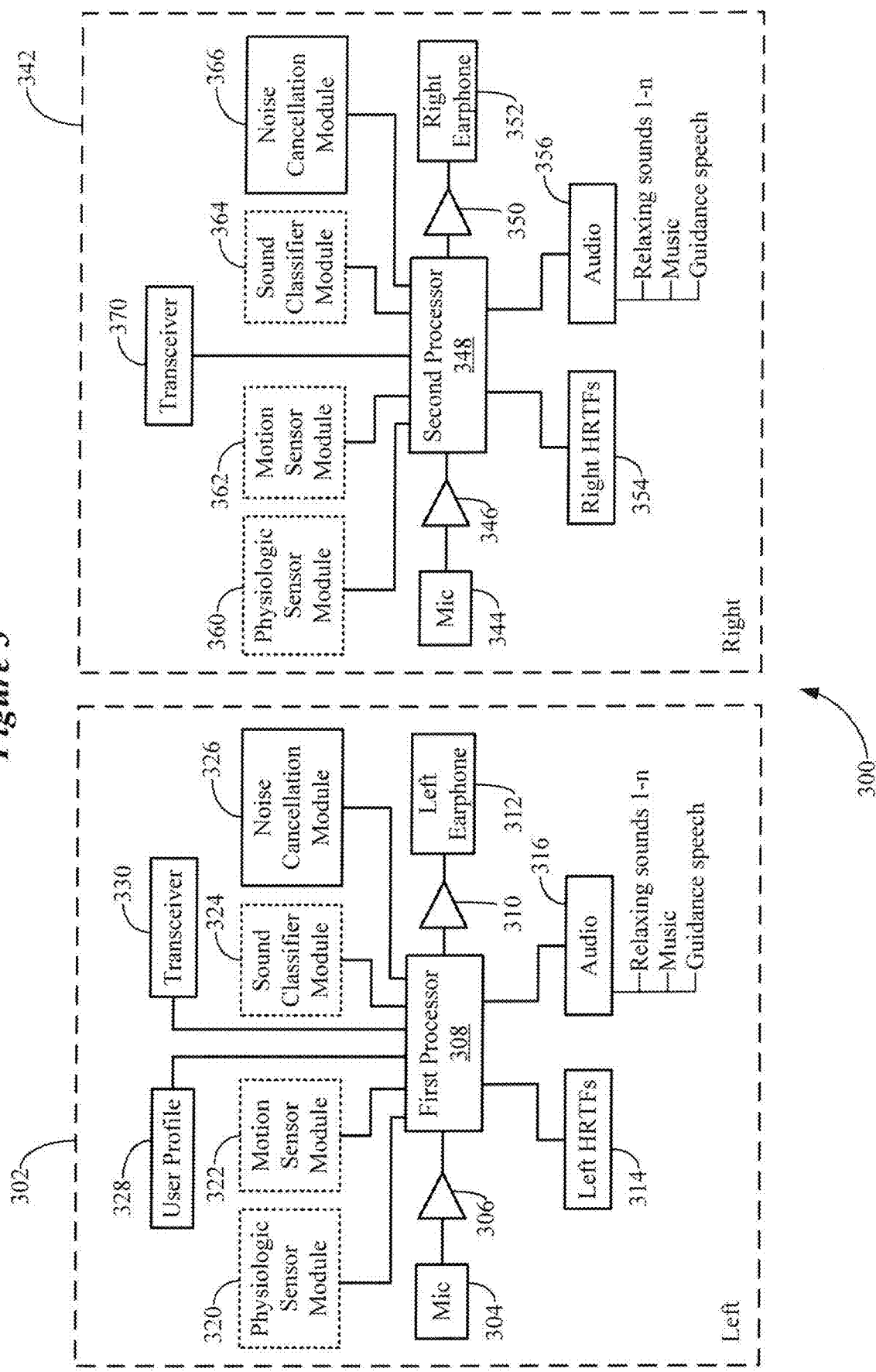
FIG. 3 is a block diagram of an ear-worn electronic device configured to conduct a predetermined mental exercise and to monitor a wearer of the device for compliance with the mental exercise in accordance with various embodiments.

FIG. 3 is a block diagram of an ear-worn electronic device 300 configured to conduct a predetermined mental exercise and to monitor a wearer of the device for compliance with the mental exercise in accordance with various embodiments. For example, the ear-worn electronic device 300 shown in FIG. 3 can be configured to implement the methods shown in FIGS. 1 and 2. The ear-worn electronic device 300 can be configured to determine the effectiveness of a predetermined mental exercise performed by the wearer. The ear-worn electronic device 300 includes a left ear device 302 and a right ear device 342. The left ear device 302 includes a first processor 308 coupled to a transceiver 330.

The right ear device 342 includes a second processor 348 coupled to a transceiver 370. The first and second processors 308 and 348 can each be representative of a single processor or multiple processors. The term processor can encompass a multi-core processor, a DSP, an audio processor or a combination of these processors. It is understood that the first and second processors 308 and 348 incorporate or are otherwise coupled to memory.

The first and second processors 308 and 348 are communicatively coupled via transceivers 330 and 370. Preferably, the transceivers 330 and 370 are wireless transceivers, such as BLE or WiFi® transceivers or NFMI devices. In some embodiments, the first and second processors 308 and 348 can be communicatively coupled via a wired connection. The first and second processors 308 and 348 operate cooperatively to produce a 3-D rendered acoustic space within which relaxing sounds and verbal instructions are provided for guiding a wearer of the device 300 through a mental exercise within the 3-D rendered acoustic space.

The left ear device 302 includes a microphone 304, which can be a single or multiple microphones (e.g., a microphone array). The microphone 304 is coupled to a preamplifier 306, the output of which is coupled to the first processor 308. An audio output of the first processor 308 is coupled to an amplifier 310 which is coupled to a left earphone 312. The right ear device 342 includes a microphone 344, which can be a single or multiple microphones (e.g., a microphone array). The microphone 344 is coupled to a preamplifier 346, the output of which is coupled to the second processor 348. An audio output of the second processor 348 is coupled to an amplifier 350 which is coupled to a right earphone 352.

The ear-worn electronic device 300 generates various sounds within a 3-D rendered acoustic space created for conducting a mental exercise by a wearer of the device 300. As shown in FIG. 3, each of the left and right devices 302 and 342 can be configured to generate audio 316 and 356, which can include a number of different relaxing sounds, music and guidance speech. The audio 316, 356 can be stored in a memory of the left and right devices 302, 342. In some embodiments, audio is stored in only one of the left and right devices 302, 342 and transmitted to the other of the left and right devices 302, 342 via the transceivers 330, 370. In other embodiments, some or all of the audio 316, 356 can be streamed from an external device to one or both transceivers 330, 370 of the ear-worn electronic device 300. For example, some or all of the audio 316, 356 can be received by one or both transceivers 330, 370 from an assistive listening system, a TV streamer, a radio, a smartphone, a laptop, a cell phone/entertainment device or other electronic device that serves as a source of digital audio data.

The audio 316, 356 can include one or more relaxing sounds, such as the sound of rain, wind, ocean waves, or bird calls. The audio 316, 356 can also include music or tones, such as slow-tempo acoustic music, ambient music, world music (e.g., Native American flute), slow-tempo electronic symphonies, Chakra Chants or other chants, and binaural beats (e.g., a 250 Hz tone played in the right ear and a 260 Hz tone played in the left ear). The audio 316, 356 also includes guidance speech which is typically synthesized speech, but may also be pre-recorded human speech.

The left and right ear devices 302 and 342 include a physiologic sensor module 320 and 360 coupled to the first and second processors 308 and 348. In some embodiments, only one of the left and right ear devices 302, 342 includes a physiologic sensor module 320 or 360. The physiologic sensor modules 320, 360 include one or more physiologic sensors that sense one or more physiologic signals or conditions of the wearer during a mental exercise directed by the guidance speech. As previously discussed, one or more sensors of the physiologic sensor modules 320, 360 can be housed in the left ear device 302, the right ear device 342, or distributed between the left and right ear devices 302, 342 of the ear-worn electronic device 300.

According to various embodiments, the physiologic sensor modules 320, 360 (or single module 320 or 360) are configured to monitor the mental state of the wearer during the mental exercise. In other embodiments, the physiologic sensor modules 320, 360 (or single module 320 or 360) are configured to monitor the physical state of the wearer during the mental exercise. In further embodiments, the physiologic sensor modules 320, 360 (or single module 320 or 360) are configured to monitor both the mental state and the physical state of the wearer during the mental exercise. A non-exhaustive, representative list of physiologic signals or conditions of the wearer that can be sensed and monitored by the physiologic sensor modules 320, 360 (or single module 320 or 360) includes brain activity, heart activity, breathing activity, body temperature, electrodermal activity, eye movement, and blood pressure. Readings from the physiologic sensor modules 320, 360 (or single module 320 or 360) can be extracted periodically during the mental exercises and also at times outside of the exercises.

The ear-worn electronic device 300 includes motion sensor modules 322 and 362 coupled to the first and second processors 308 and 348. In some embodiments, only one of the left and right ear devices 302, 342 includes a motion sensor module 322 or 362. The motion sensor modules 322, 362 include one or more motion sensors that sense movement of the wearer during a mental exercise directed by the guidance speech. As discussed above, one or more sensors of the motion sensor modules 322, 362 can be housed in the left ear device 302, the right ear device 342, or distributed between the left and right ear devices 302 and 342 of the ear-worn electronic device 300. The motion sensor modules 322, 362 (or single module 322 or 362) are configured to track movement of the wearer for a variety of purposes. For example, auditory objects of the soundscape created by the ear-worn electronic device 300 can change in an interactive and realistic manner based on the wearer's movements which are tracked by the motion sensor modules 322, 362 (or single module 322 or 362). For example, the spatial location of a waterfall within the soundscape remains static (e.g., in the same place) as the wearer moves his or her head during the mental exercise. As another example, the first and second processors 308, 348 (or a single processor 308 or 348) can operate cooperatively with the motion sensor modules 322, 362 (or single module 322 or 362) to determine if user movement during the mental exercise is consistent with verbal instructions provided by the guidance speech. Reinforcing or corrective commentary can be provided depending on whether or not the wearer's tracked movement is consistent with verbal instructions provided by the guidance speech.

In some embodiments, each of the left and right ear devices 302 and 342 can include a noise cancellation module 326 and 366 configured to provide active noise cancellation to create a quiet 3-D rendered acoustic space. According to these and other embodiments, each of the left and right ear devices 302 and 342 can also include a sound classifier module 324 and 364. In some embodiments, only one of the left and right ear devices 302, 342 includes a sound classifier module 324 or 364. The sound classifier modules 324, 364 (or single module 324 or 364) can be configured to provide environmental awareness of external events that occur in the acoustic environment surrounding the wearer during performance of a mental exercise. As was discussed previously, there are often plenty of potentially distracting events and important events that can interfere with the proper execution of a mental exercise when the location used for performing the mental exercise is not a place originally designed for that purpose. The sound classifier modules 324, 364 (or single module 324 or 364) are configured to classify a sound of interest received by the ear-worn electronic device 300 during the mental exercise. In response to the sound classification provided by the sound classifier modules 324, 364 (or single module 324 or 364), the first and second processors 308, 348 (or single processor 308 or 348) can generate verbal commentary suggesting that the wearer ignore or consider the sound of interest. For example, a car horn may be considered to be a distracting sound, which may cause the first and second processors 308, 348 (or single processor 308 or 348) to verbally instruct the wearer to ignore the external sound. A ringing telephone may be considered to be an important sound, which may cause the first and second processors 308, 348 (or single processor 308 or 348) to verbally instruct the wearer to pause the mental exercise and take notice of the external sound.

According to some embodiments, the first and second processors 308, 348 can be configured to implement noise cancellation based on the classification of an external sound. For example, the first and second processors 308, 348 can be configured to implement a noise cancellation algorithm to either cancel or pass a sound of interest based on the classification of the sound of interest. In the case of the car horn example discussed above, the first and second processors 308, 348 in cooperation with the noise cancellation modules 326, 366, can cancel the car horn sound so as not to distract the wearer during performance of the mental exercise. In the case of the ringing telephone, the first and second processors 308, 348 and the noise cancellation modules 326, 366 can cooperate to pass the sound of the ringing telephone so as to alert the wearer of an incoming phone call.

The ear-worn electronic device 302 includes a user profile 328 stored in a memory of the device 302. The user profile 328 can be stored in both of the left and right devices 302, 342 or only one of the devices 302, 342. For simplicity, the user profile 328 is included in the left ear device 302. The user profile 328 stores a variety of information relating to the implementation and execution of the mental exercises, including the soundscapes, music, exercises, and guidance speech, and wearer response information such as physiologic response data and preferences. As will be discussed below, a wearer's user profile 328 can be modified over time to enhance the wearer's experience and performance.

Figure 4:
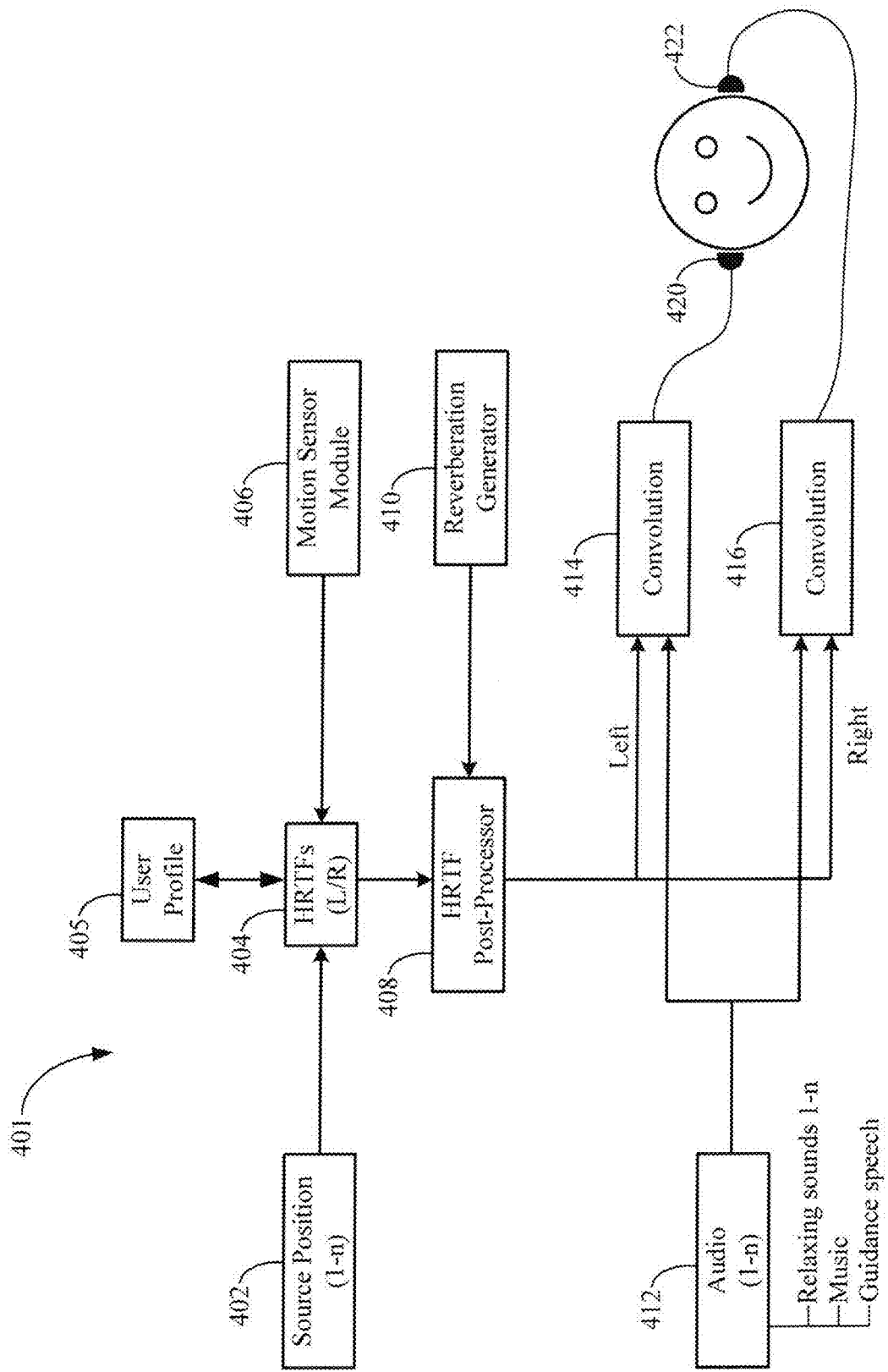
FIG. 4 is a functional block diagram of an ear-worn electronic device in accordance with various embodiments.

FIG. 4 shows an audio rendering subsystem 401 of the ear-worn electronic device, such as that shown in FIG. 3, which creates a 3-D rendered acoustic space with music and other relaxing sounds for conducting a mental exercise performed by a wearer in accordance with various embodiments. With reference to FIG. 3, the functions performed by the audio rendering subsystem 401 shown in FIG. 4 are implemented by the left and right ear devices 302 and 342 (via the communicatively coupled first and second processors 308 and 348) operating cooperatively. In some embodiments, the components and functionality shown in FIG. 4 are incorporated in each of the left and right ear devices 302 and 342. In other embodiments, selected components and functionality shown in FIG. 4 can be incorporated in one, but not both, of the left and rear ear devices 302 and 342.

As was discussed previously, the ear-worn electronic device generates a number of different sounds, including relaxing sounds, music, and guidance speech. These sounds are binaurally rendered by the audio rendering subsystem 401 to create a 3-D sound sensation for the wearer when played back through left and right earphones 420 and 422 of the ear-worn electronic device. As is shown in FIG. 4, the audio rendering subsystem 401 can generate or receive a number (1-n) of different audio sounds 412, including relaxing sounds, music, and guidance speech. Each of these audio sounds 412 can be located at a specific source position 402 within a 3-D rendered acoustic space. Locating the source position 402 of the various audio sounds 412 can involve defining the loudness of a sound within the 3-D rendered acoustic space. The loudness of a sound can be adjusted as a function of distance between the source of the sound and the wearer (e.g., a distant waterfall versus a nearby chirping bird). The source positions 402 of the audio sounds 412 are determined by left and right head-related transfer functions (HRTFs) 404.

HRTFs characterize how a person's head, ears, and torso spectrally shape sound waves received in the person's ear. The spectral shaping of the sound waves provides spatialization cues that enable the hearer to position the source of the sound. Incorporating spatialization cues based on the HRTF of the hearer into electronically produced sounds (audio sounds 412) allows the hearer to identify the location 402 of the sound source. An HRTF data set is the aggregation of multiple HRTFs for multiple directions around the individual's head that summarizes the location dependent variation in the pressure waves of the acoustic signal. For convenience, this disclosure may refer to a data set of HRTFs simply as an "HRTF" with the understanding that the term "HRTF" as used herein refers to a data set of one or more HRTFs corresponding respectively to one or multiple directions.

Spatialization cues are highly individualized and include the coloration of sound, the time difference between sounds received at the left and right ears, referred to as the interaural time difference (ITD), and the sound level difference between the sounds received at the left and right ears, referred to as the interaural level difference (ILD) between ears. Sound coloration is largely dependent on the shape of external portion of the ear and allows for vertical localization of a sound source in the vertical plane while the ITD and ILD allow for localization of the sound source in the horizontal plane.

Virtual sounds, such as those produced by the audio rendering subsystem 401, are electronically generated sounds that are delivered to a wearer's ear by the left and right earphones 420 and 422. The virtual sounds are delivered by a speaker that converts the electronic representation of the virtual sound into acoustic waves close to the wearer's ear drum. As such, the virtual sounds are not modified by the head and ear morphology of the person wearing the ear-worn electronic device. However, spatialization cues that mimic those which would be present in an actual sound that is modified by the head and ear morphology can be included in the virtual sound. These spatialization cues enable the wearer of the ear-worn electronic device to locate the source of the virtual sound in the 3-D rendered acoustic space. Spatialization cues can give the user the auditory experience that the sound source is in front or back, above or below, to the right or left sides of the wearer of the ear-worn electronic device.

A user profile 405 can be stored in a memory of the ear-worn electronic device. Among other information, the user profile 405 stores HRTFs 404 (e.g., an HRTF for each of the left and right earphones 420 and 422) for the wearer that are used to determine the source position 402 of each audio sound 412. In some embodiments, the HRTF stored in the user profile 452 is a non-individualized HRTF (e.g., a generic or idealized HRTF), which can be satisfactory for most wearers. In other embodiments, the HRTF stored in the user profile 452 is an HRTF that has been individualized for the wearer of the ear-worn electronic device. One technique for developing an individualized HRTF is disclosed in commonly owned U.S. patent application Ser. No. 15/331,230 filed on Oct. 21, 2016, which is incorporated herein by reference.

Location processing of the source positions 402 applies the stored HRTFs 404 to the audio sound 412 to locate each sound within the 3-D rendered acoustic space. Using data received from the motion sensor module 406, the location processing tracks movement of the wearer (e.g., the wearer's head) and maintains proper positioning of each sound within the 3-D rendered acoustic space via adjustments to the HRTFs 404. As the wearer's head moves, for example, the HRTFs 404 are adjusted so that the source positions 402 of the various audio sounds 412 within the 3-D rendered acoustic space are maintained (e.g., a waterfall location remains static at its intended position while the wearer moves his or her head).

The audio rendering subsystem 401 includes an HRTF post-processor 408 coupled to an output of the HRTFs 404 and a reverberation generator 410. The HRTF post-processor 408 can include a rendering filter. Controlling reverberation is important to producing an immersive and realistic 3-D sensation. The reverberation generator 410 provides for adjustment of reverberation to reproduce desired acoustics of the 3-D rendered acoustic space.

The audio rendering subsystem 401 is configured to produce binaurally render teach of the audio sounds 412 by performing a convolution 414 on an audio sound 412 and the left HRTF and a convolution 416 on the audio sound 412 and the right HRTF. The binarualized audio sound 412 is communicated to the left and right earphones 420 and 422 of the ear-worn electronic device. This process is performed for each of the audio sounds 412 to be presented in the 3-D rendered acoustic space.

Figure 5:
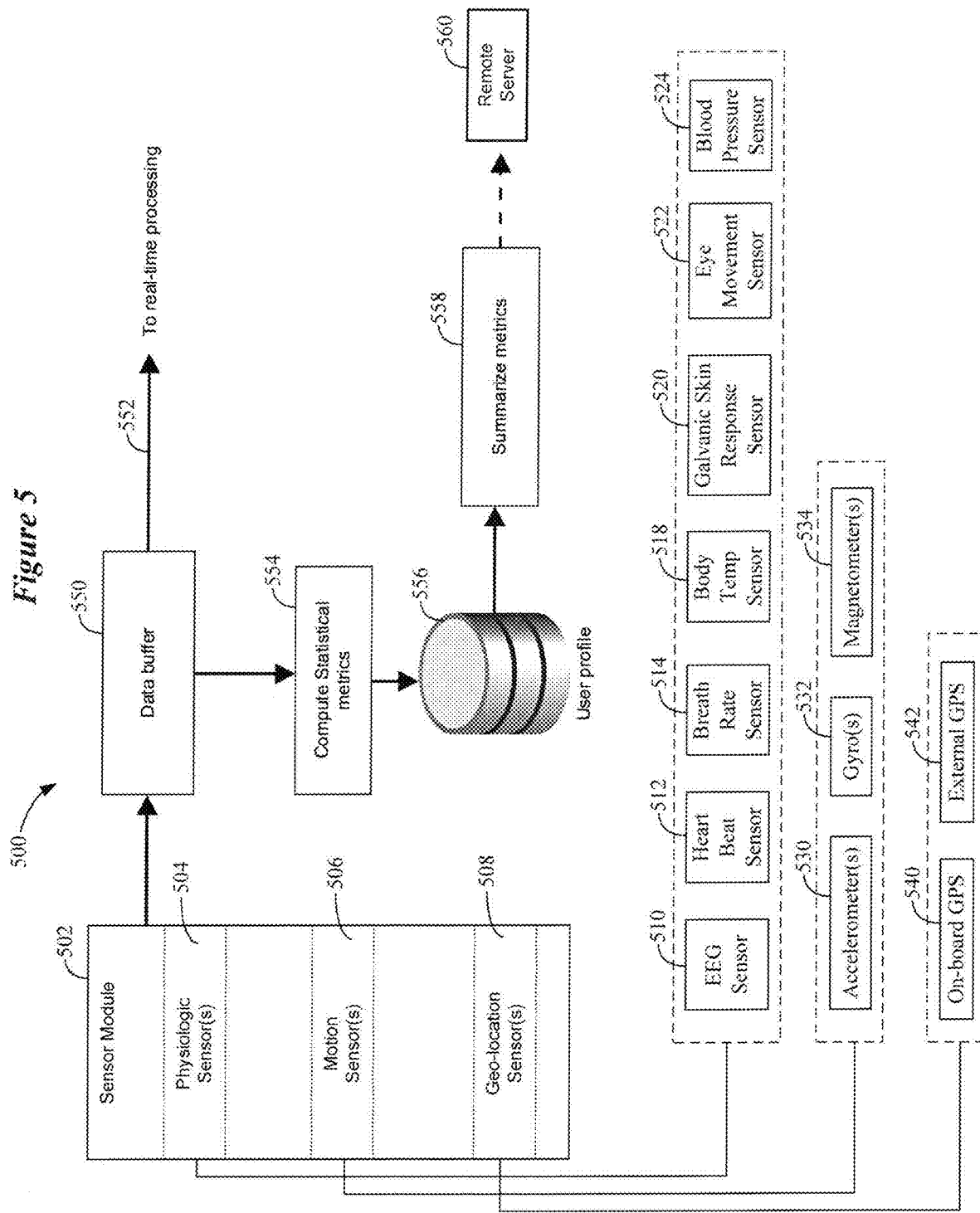
FIG. 5 illustrates a sensor module of an ear-worn electronic device in accordance with various embodiments.

FIG. 5 illustrates a sensor module of an ear-worn electronic device in accordance with various embodiments. According to some embodiments, the sensor module 502 of the ear-worn electronic device 500 includes one or more physiologic sensors 504 and one or more motion sensors 506. According to other embodiments, the sensor module 500 can include one or more geo-location sensors 508 in addition to the physiologic and motion sensors 504 and 506. The physiologic sensors 504 can include one or more of an electroencephalograph (EEG) sensor 510, a heartbeat sensor 512 (e.g., pulse oximeter), a breath rate sensor 514, a body temperature sensor 518, a galvanic skin response sensor 520, and an eye movement (electrooculogram) sensor 522. In some embodiments, an external blood pressure sensor 524 can be communicatively linked to the ear-worn electronic device (e.g., via a BLE link). The eye movement sensor 522 may be, for example, an electrooculographic (EOG) sensor, such as an EOG sensor disclosed in commonly owned U.S. Pat. No. 9,167,356, which is incorporated herein by reference.

The motion sensors 506 can include one or more of accelerometers 530, gyros 532, and magnetometers 534. For example, the motion sensors 506 can be implemented as a 9-axis sensor or an IMUs (inertial measurement unit). A suitable IMU is disclosed in commonly owned U.S. patent application Ser. No. 15/331,230, filed Oct. 21, 2016, which is incorporated herein by reference. As was discussed previously, a single motion sensor can be housed in one of the left and right ear devices of the ear-worn electronic device 500. Alternatively, dual motion sensors can be employed, with one motion sensor housed in each of the left and right devices of the ear-worn electronic device 500. The geo-location sensors 508 can include one or both of an onboard GPS 540 or an external GPS 542 (e.g., a GPS of a smart phone communicatively linked to the ear-worn electronic device via a BLE link).

Data produced by the various sensors 504, 506, 508 of the sensor module 502 is communicated to a data buffer 550. The data stored in the data buffer 550 is provided at an output 552, which is coupled to downstream components that provide for real-time processing of the data (e.g., for sound location processing shown in FIG. 4; mental and/or physical state assessment in FIG. 3; locating the wearer). The data stored in the data buffer 550 is also processed to compute various statistical metrics 554. For example, the mean, median, standard deviation, minimum, and maximum represent statistical metrics can be computed for each sensor of the sensor module 502. These statistical metrics can be extracted and stored periodically in a user profile 556. A summary of these statistical metrics 558 can be communicated to a remote server 560 via a transceiver (e.g., BLE transceiver) of the ear-worn electronic device 500.

Figure 6:
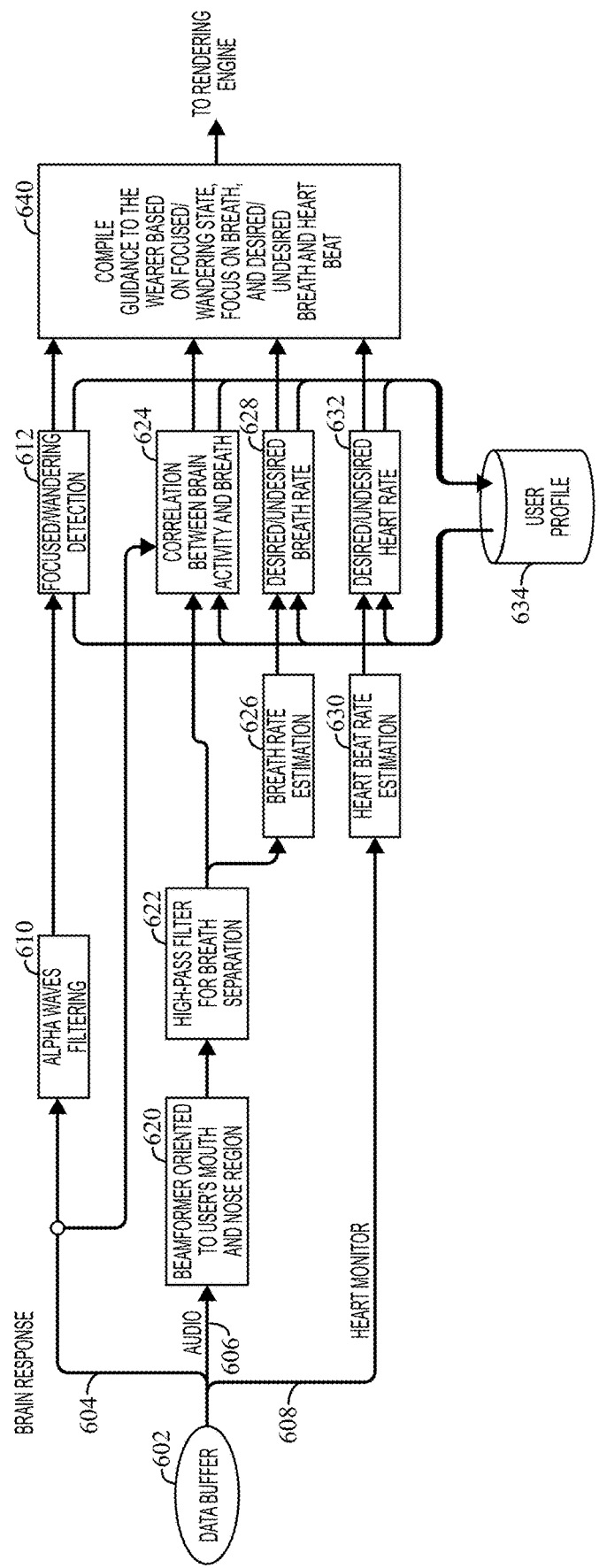
FIG. 6 is a functional block diagram showing how data produced by sensors of an ear-worn electronic device can be processed to monitor a wearer's compliance with a predetermined mental exercise in accordance with various embodiments.

FIG. 6 is a functional block diagram showing how data produced by sensors of an ear-worn electronic device can be processed to monitor a wearer's compliance with a predetermined mental exercise in accordance with various embodiments. During a mental exercise, such as a mindfulness exercise, speech instructions are rendered by the ear-worn electronic device to guide the wearer through the exercise. According to some embodiments, the level of detail of the speech instructions can be adjusted based on the wearer's preference, which is reflective of the wearer's expertise with performing the mental exercise. For example, a detailed level of speech instructions can be provided to a wearer having little or no experience with a particular mental exercise. As the wearer gains experience with the particular mental exercise, the wearer may wish to reduce the level of speech instruction detail, which can otherwise be considered distracting to the more experienced wearer.

While speech instructions are played back to the wearer, readings from the various sensors of the ear-worn electronic device are accessed periodically and, depending on the mental and/or physical state information that can be inferred from those readings, the speech instructions can be adjusted in response to the mental and/or physical state information. For example, information derived from the sensors may indicate that the wearer is complying with the speech instructions for a particular mental exercise, which can result in playing back reinforcing (e.g., supportive) speech (e.g., "good job"). In some embodiments, the level of speech instruction detail can be reduced in response to the sensors indicating that the wearer is complying with the speech instructions for the particular mental exercise. If the information derived from the sensors indicates that the wearer is not complying with the speech instructions for the particular mental exercise, corrective (e.g., encouraging) speech can be played back to help the wearer comply with the parameters of the particular mental exercise (e.g., "your breath rate is high—focus on your breathing"). In some embodiments, the level of speech instruction detail can be increased in response to the sensors indicated that the wearer is not complying with the speech instructions for the particular mental exercise.

As was discussed previously, data from the various sensors of the ear-worn electronic device is stored in a data buffer 602. In the representative example shown in FIG. 6, the data buffer 602 includes brain response data 604, audio 606 from microphones, and heart monitoring data 608. The brain response data 604, which can be acquired by an EEG sensor of the ear-worn electronic device, is filtered 610 so that alpha waves can be processed and evaluated to determine whether the wearer's mental state is focused or wandering. The brain response data 604 typically contains various information contained within different frequency bands, such as the delta band (1-4 Hz), theta band (4-8 Hz), and alpha band (8-12 Hz).

The alpha band refers to rhythmic oscillatory brain activity within the frequency range of 8 to 12 Hz. Alpha waves have several functional correlations to sensory, motor, and memory functions. The level of alpha band power corresponds to the degree of mental and physical relaxation of the wearer of the ear-worn electronic device. For example, increased levels of alpha band power result during mental and physical relaxation with eyes closed. In particular, alpha band power increases during relaxing mental exercises, such as meditation. By contrast, alpha band power is reduced, or suppressed, during mental or bodily activity with eyes open. Alpha wave suppression indicates that the brain is gearing up to receive information from various senses, coordinating attentional resources, and focusing on events occurring at a particular moment.

According to various embodiments, an ear-worn electronic device uses filtered alpha waves 610 to determine whether the wearer is focused on the mental exercise or is experiencing mind wandering during the mental exercise. For example, the magnitude of the alpha waves can be periodically measured. Relative changes in alpha wave magnitude can be computed and compared to a threshold to detect 612 whether the wearer is focused or experiencing mind wandering. The threshold can be an average alpha wave magnitude computed during the mental exercise or a previous mental exercise. The alpha wave threshold can be stored in a user profile 634. In some embodiments, the user profile 634 stores a high threshold and a low threshold, both of which can be derived for the particular wearer or from a population of wearers. Alpha wave magnitudes that are equal to or higher than the high threshold indicate that the wearer is focused on the mental exercise. Alpha wave magnitudes that are equal to or lower than the low threshold indicate that the wearer's mindfulness is wandering.

During the mental exercise, the measured alpha wave magnitude is compared to the high and low thresholds to detect 612 wearer focus and wandering. Depending on the measured alpha wave magnitude, the ear-worn electronic device provides different types of audio guidance 640 via the audio rendering subsystem. For example, every time the high threshold is met or exceeded, positive audio feedback (e.g., sounds, music, and/or speech) can be provided to the wearer. Every time the low threshold is met or exceeded, guidance speech can be provided to encourage the wearer to be aware of mind wandering. The guidance speech, for example, can encourage the wearer to focus on the wearer's breathing. The positive audio feedback and the guidance speech can be adjusted based on the preferences and expertise of the wearer.

According to some embodiments, one or more microphones of the ear-worn electronic device can be used to detect the wearer's breathing. As shown in FIG. 6, audio 606 from microphones (e.g., a microphone array) can be used to detect breathing of the wearer, which can be tracked by the ear-worn electronic device. In some embodiments, a beam-forming technique 620 can be used to orient the microphones toward the wearer's mouth and nose region. For example, source separation can be performed to isolate sounds emanating from the direction of the wearer's mouth and nose. High-pass filtering 622 can be used to isolate respiratory specific sounds. The wearer's breath rate (e.g., breaths per minute) can be estimated 626 based on the respiratory specific sounds. The wearer's breath rate can be compared to a threshold stored in the user profile 634 to distinguish between a desired and undesired breath rate 628 for the mental exercise, and appropriate guidance speech and positive audio feedback 640 can be provided to the wearer based on the comparison.

In some embodiments, a preset range of relaxed breath rates can be based on the user profile 634, a population profile, or combination of these profiles. The preset range of relaxed breath rates can be used to trigger guidance speech and audio feedback in the form of music, sounds, and/or speech to instruct the user to relax his or her breathing rate. For example, in response to the breath rate exceeding the threshold (e.g., high breath rate), guidance speech can be provided to encourage the wearer to focus on his or her breathing. In response to the breath rate falling below the threshold (e.g., an appropriate breath rate), positive audio feedback can be periodically provided to the wearer.

According to some embodiments, an association between the wearer's brain activity (e.g., EEG signal) and breathing can be determined by the ear-worn electronic device. For example, a correlation between the wearer's brain activity and breathing can be computed by the ear-worn electronic device. The computed correlation (or other association) can be used to quantify how much the wearer is actually focusing on his or her breathing. For example, if the computed correlation falls below a threshold for the wearer (e.g., stored in the user profile 634), guidance speech can be provided to help the wearer focus on his or her breathing. If the computed correlation exceeds the threshold, positive audio feedback can be periodically provided to the wearer.

As is further shown in FIG. 6, the data buffer 602 can store heart monitoring information 608 acquired from the sensor module of the ear-worn electronic device. For example, the heart monitoring information 608 can be acquired from a heartbeat or heart rate sensor of the ear-worn electronic device. Using the heart monitoring information 608, the wearer's heart rate can be estimated 630. The wearer's heart rate can be compared against a threshold stored in the user profile 634 to distinguish 632 between a desired and an undesired heart rate for the particular mental exercise. This threshold can be unique to the wearer or established from population data. In response to the heart rate exceeding the threshold (e.g., high heart rate), guidance speech can be provided to encourage the wearer to focus on his or her breathing. In response to the heart rate falling below the threshold (e.g., an appropriate heart rate), positive audio feedback can be periodically provided to the wearer.

Figure 7:
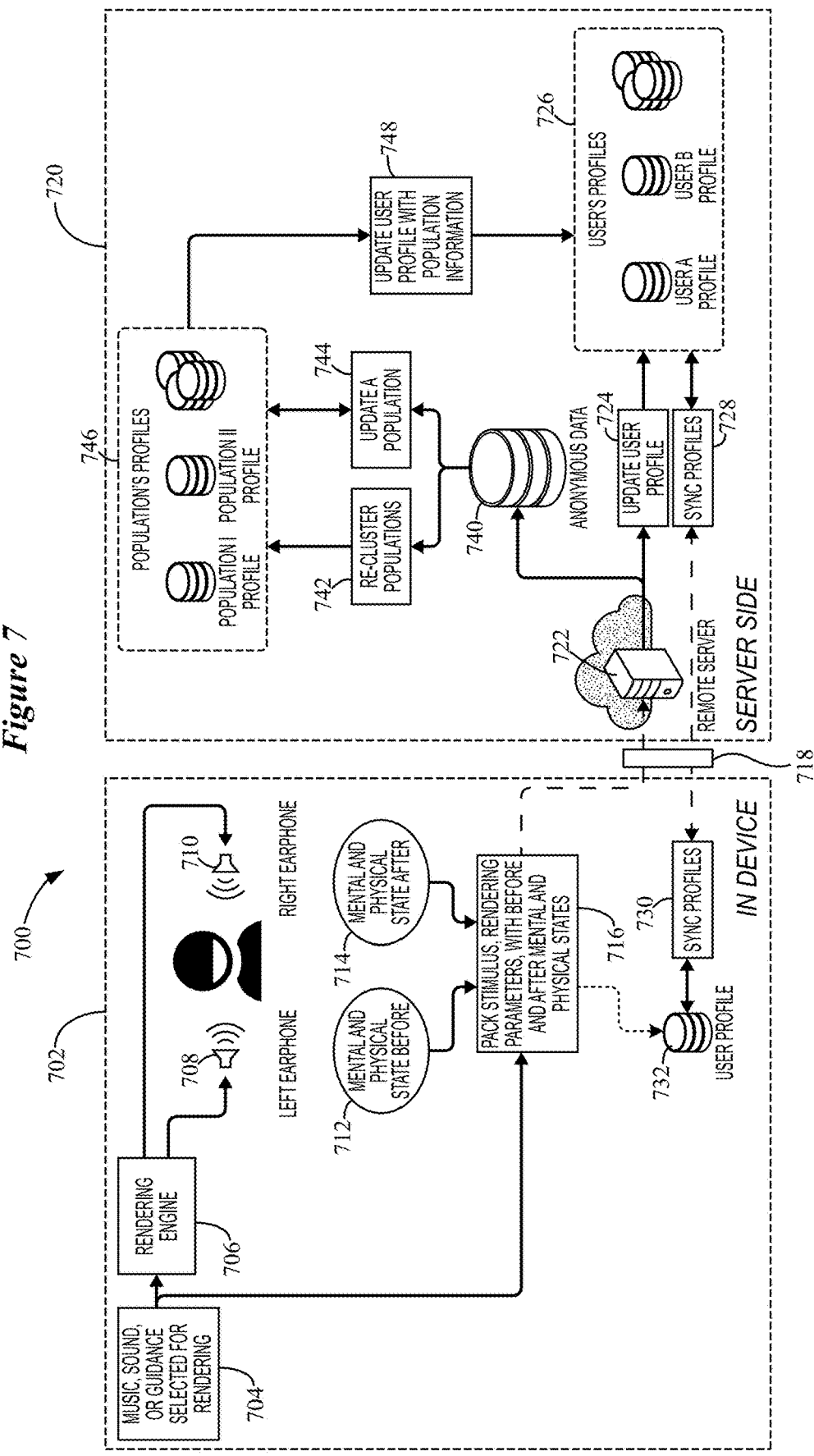
FIG. 7 is a functional block diagram of various customization processes performed by an ear-worn electronic device alone or in cooperation with a remote server in accordance with various embodiments.

The functionality of the ear-worn electronic device can be customized over time based on the experience of a given wearer and/or a population of wearers. Customization of the ear-worn electronic device over time can be implemented solely by the ear-worn electronic device (in situ) or in cooperation with a remote server. FIG. 7 is a functional block diagram of various customization processes performed by an ear-worn electronic device alone or in cooperation with a remote server in accordance with various embodiments. In some embodiments, the customization processes 702 shown in FIG. 7 are performed by an ear-worn electronic device without interaction with a remote server. In other embodiments, the customization processes 720 shown in FIG. 7 are performed by an ear-worn electronic device in cooperation with the remote server.

Conducting and monitoring a mental exercise performed by a wearer of an ear-worn electronic device involves selecting music, sound, and/or guidance speech for rendering 704. Selecting audio content 704 for rendering can be accomplished directly through wearer interaction with an interface of the ear-worn electronic device (e.g., buttons, switches) or indirectly through a smartphone or other external device communicatively linked to the ear-worn electronic device. The selected audio content 704 is communicated to the audio rendering subsystem 706 of the ear-worn electronic device, which binauralizes the audio for presentation to the wearer via left and right earphones 708 and 710. The sensor module of the ear-worn electronic device assesses the mental and physical state of the wearer before 712 and after 714 a mental exercise is performed by the wearer. The audio content 704 selected for rendering, rendering parameters, and before/after mental and physical state data 712 and 714 can be packaged 716 and stored in a user profile 732.

Over time, the user profile 732 will continue to store data on which soundscapes, mental exercises, and verbal instructions help the specific wearer achieve optimal performance. The ear-worn electronic device can also decrease the amount of audio feedback and verbal guidance provided to the wearer as the wearer acquires expertise, which is quantitatively measured, unless the wearer modifies this behavior. This data and the user profile 732 can be stored locally within the ear-worn electronic device. In some embodiments, this data and the user profile 732 can be communicated to and stored by a remote server. Each time the ear-worn electronic device provides music, audio feedback, or verbal guidance, wearer reaction to this stimuli is monitored using sensor readings, and this data is also stored in the user profile 732. Based on past reactions to music, audio feedback, and verbal guidance, the ear-worn electronic device can adjust some or all of this stimuli within the current mental exercise or future mental exercises. For example, a level of expertise can be automatically assigned to the wearer based on sensor readings acquired during a mindfulness exercise. This level of expertise can be adjusted manually by the user or automatically by the ear-worn electronic device in response to sensor readings taken during the current or future exercises.

According to some embodiments, the audio content 704 selected for rendering, rendering parameters, and before/after mental and physical state data 712 and 714 that is packaged 716 by the ear-worn electronic device can be communicated to a remote server 722 (e.g., via a BLE or WiFi link). In various embodiments, a gateway device 718 (e.g., a smartphone, tablet, laptop or PC) serves to communicatively link the ear-worn electronic device and the remote server 722. The remote server 722 can store a multiplicity of user profiles 726. For example, the remote server 722 may receive packaged data 716 from user A. In response, the remote server 722 can update 724 the profile of user A. The remote server 722 may receive packaged data 716 from user B and, in response, update 724 the profile of user B. The remote server 722 and/or the ear-worn electronic device can synchronize 728, 730 an updated user profile 726 at the remote server 722 with a previously-generated user profile residing in the ear-worn electronic device. As such, the remote server 722 can update the user profile 732 (via the gateway device 718) stored in the ear-worn electronic device based on the packaged data 716 received by the remote server 722.

The remote server 722 can receive packaged data 716 from a multiplicity of ear-worn electronic devices, which can be stored as anonymous data 740 at the remote server 722. The anonymous data 740 collected from a population of ear-worn electronic devices can be used by the remote server 722 to customize the functionality of individual ear-worn electronic devices. The remote server 722 can create and maintain a multiplicity of population profiles 746. Periodically, and based on age, gender, location, expertise, and other demographic factors, common physiologic statistics, preferences, best-performing settings (e.g., music, sounds, verbal guidance parameters), and mental exercises are computed and summarized by the remote server 722 to form different population profiles 746 (e.g., Population I profile, Population II, profile, etc.).

As anonymous data 740 accumulates at the remote server 722, population profiles 746 can be updated 744 with newly received packaged data 716. In some cases, the remote server 722 can re-cluster the populations 742, which can result in creation of new population profiles 746 or elimination of antiquated population profiles 746. According to some embodiments, the remote server 722 can update 748 a particular user's profile (e.g., user A profile) with population information from an appropriate population profile 746 (e.g., based on age, gender, location, etc.). The population data stored at the remote server 722 can be accessed by individual ear-worn electronic devices using Internet connectivity (e.g., via gateway device 718), but can also be pre-loaded in the ear-worn electronic device and be accessed locally.

For example, the remote server 742 can be configured to learn preferences (e.g., mental exercise selection, music selection, relaxing sound selection, expertise level, guidance speech preferences, etc.) based on data produced by numerous ear-worn electronic devices and accumulated for each of the population profiles 746. These preferences can be learned by the remote server 722 based on wearer age, gender, location, etc. for each of the different population profiles 746 The remote server 742 can be configured to make recommendations for a particular wearer based on the preferences learned from the population profiles 746. In response to acceptance of a recommendation, the wearer's user profile 726 can be updated by the remote server 722. The updated user's profile can be synchronized 728, 730 so that the user's ear-worn electronic device implements the most current user profile 732. As such, a wearer's mental exercise experience can be tailored over time based on population profile information.

Figure 8:
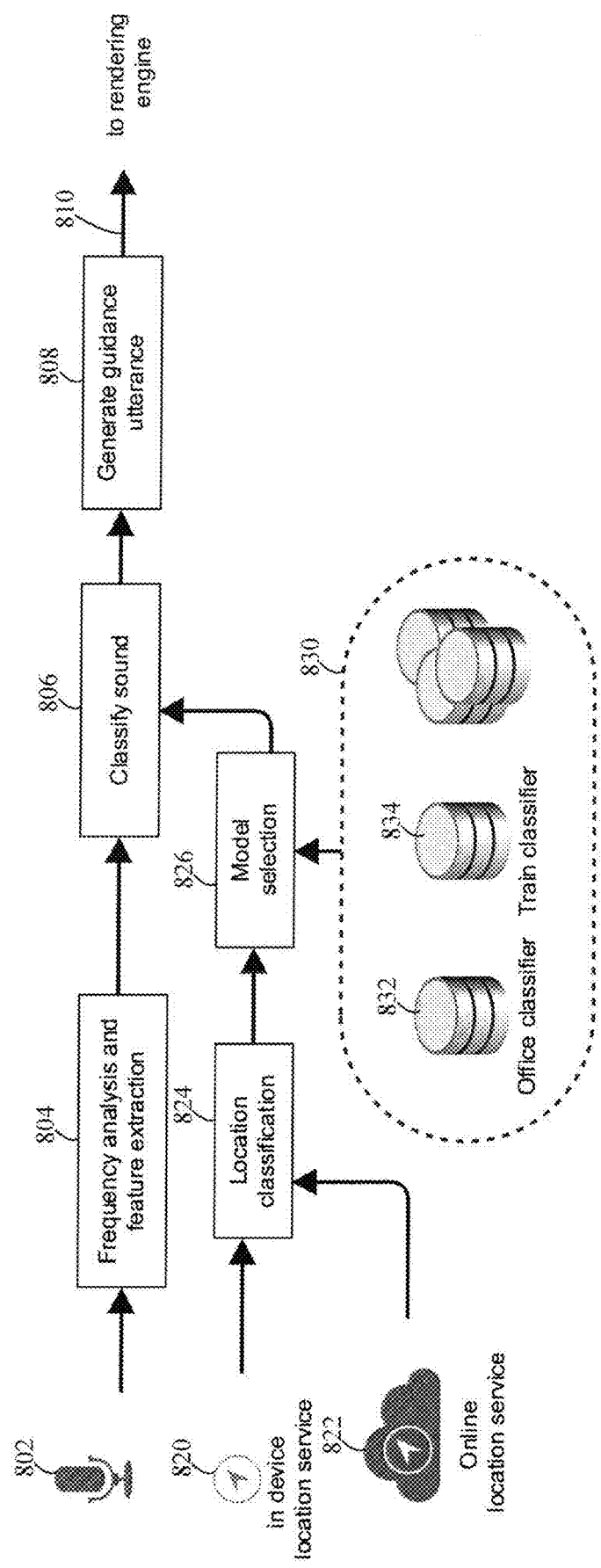
FIG. 8 is a functional block diagram involving processes for classifying sounds of interest by an ear-worn electronic device in accordance with various embodiments.

According to various embodiments, the acoustic environment surrounding the wearer of an ear-worn electronic device is monitored to identify events that can be either potentially distracting or are important requiring wearer attention. FIG. 8 is a functional block diagram involving processes for classifying sounds of interest by an ear-worn electronic device in accordance with various embodiments. One or more microphones 802 of the ear-worn electronic device monitor the acoustic environment surrounding the wearer and provide a real-time audio feed to a sound classifier module of the ear-worn electronic device (see, e.g., FIG. 3). The sound classifier module performs frequency analysis and feature extraction 804 on the real-time audio feed, which are used by a neural network classifier to classify 806 sounds of interest. The set of sounds of interest that can be classified can be closed, but can be updated and increased in number, along with the neural network classifier parameters using Internet connectivity to enable the sound classifier module to identify new sounds.

In general, the sounds of interest identified by the sound classifier module can be one of two types: a potentially distracting sound (e.g., a car passing by at the street, kids playing at a park, etc.) or a sound important to the wearer (e.g., the wearer's name being called, a phone ringing at work, a train arriving at a train station). When the sound of interest is potentially distracting, guidance 808 in the form of speech or a masking sound can be provided to the wearer to help the wearer ignore the sound. When the sound is important to the wearer, guidance 808 indicating that such a sound is occurring can be provided to allow the wearer to decide if he or she wants to interrupt the mental exercise session. The mental exercise session can be paused or terminated by wearer actuation of a button or switch of the ear-worn electronic device. In some embodiments, a button or icon on a display of an external device (e.g., a smartphone) communicatively linked to the ear-worn electronic device can be activated by the wearer. After the interruption, the mental exercise session can be resumed by actuation of an appropriate button, switch or icon by the wearer.

According to some embodiments, the ear-worn electronic device incorporates a geo-location device 820 (e.g., a GPS sensor) or has access to an online location service 822 via a wireless link and an Internet connection. Using the geo-location data, the ear-worn electronic device can perform location classification 824 that identifies the geo-location of the wearer. The ear-worn electronic device can store a multiplicity of classification models 830. Each of the classification models can be specific for a particular geo-location. Based on the location classification 824, an appropriate model can be selected 826 for use by the sound classifier module when classifying a sound of interest 806. For example, if the geo-location subsystem of the ear-worn electronic device identifies the current location of the wearer as outdoor, a sound classification model that only includes outdoor sounds will be selected 826. If the geo-location subsystem identifies the current location of the wearer as a train station or a moving train, then a train specific sound classification model will be selected 826. Other geo-locations, such as the wearer's home or place of work, can be preset by the wearer.

According to some embodiments, an ear-worn electronic device can be configured with a wireless transceiver (e.g., a BLE or WiFi® transceiver) to communicate with one or more external sensors and/or wearable devices. Connecting to one or more external sensors and/or wearable devices can expand the capabilities of the wearer's ear-worn electronic device. Examples of such external sensors/wearable devices include additional devices incorporating EEG sensors placed around the head or as a cap or helmet. One or more temperature sensors can be deployed at different locations of the body to sense skin temperature. Also, one or more galvanic skin response sensors can be deployed at different locations of the body, such as for measuring stress of the wearer. Various sensors (e.g., those disclosed herein) can be embedded in objects like clothing or a yoga mat to provide more accurate measurements of body posture. A peer network can be established between the ear-worn electronic device and the external sensors/wearable devices. In some embodiments, each of a multiplicity of ear-worn electronic devices can incorporate a wireless transceiver that can be connected via a peer network. Data produced by and/or stored in the ear-worn electronic devices can be shared between wearers and/or an exercise instructor/monitor in a group session environment (e.g. a group meditation session).

FIG. 9 is a block diagram showing various components of an ear-worn electronic device 902 that can be configured to conduct and monitor a mental exercise performed by a wearer of the device in accordance with various embodiments. The block diagram of FIG. 9 represents a generic ear-worn electronic device for purposes of illustration. It is understood that an ear-worn electronic device 902 may exclude some of the components shown in FIG. 9 and/or include additional components. It is also understood that the ear-worn electronic device 902 illustrated in FIG. 9 can be either a right ear-worn device or a left-ear worn device. The components of the right and left ear-worn devices can be the same or different. For example, in some embodiments, only one of the right and left ear-worn devices includes physiologic sensors (or motion sensors). In other embodiments, the right and left ear-worn devices can include one or more physiologic sensors (or motion sensors).

The ear-worn electronic device 902 shown in FIG. 9 includes several components electrically connected to a mother flexible circuit 903. A battery 905 is electrically connected to the mother flexible circuit 903 and provides power to the various components of the ear-worn electronic device 902. One or more microphones 906 are electrically connected to the mother flexible circuit 903, which provides electrical communication between the microphones 906 and a DSP 904. Among other components, the DSP 904 incorporates or is coupled to audio signal processing circuitry configured to perform the functions of the audio rendering subsystem described in the disclosure. One or more user switches 908 (e.g., on/off, volume, mic directional settings, mode selection) are electrically coupled to the DSP 904 via the flexible mother circuit 903.

An audio output device 910 is electrically connected to the DSP 904 via the flexible mother circuit 903. In some embodiments, the audio output device 910 comprises a speaker (coupled to an amplifier). In other embodiments, the audio output device 910 comprises an amplifier coupled to an external receiver 912 adapted for positioning within an ear of a wearer. The ear-worn electronic device 902 may incorporate a communication device 907 coupled to the flexible mother circuit 903 and to an antenna 909 directly or indirectly via the flexible mother circuit 903. The communication device 907 can be a Bluetooth® transceiver, such as a BLE (Bluetooth® low energy) transceiver or other transceiver (e.g., an IEEE 802.11 compliant device). The communication device 907 can be configured to communicate with an external device, such as a smartphone or laptop, in accordance with various embodiments.

This document discloses numerous embodiments, including but not limited to the following:

Item 1 is a method implemented by an ear-worn electronic device configured to be worn by a wearer and comprising a right ear device and a left ear device, the method comprising:

producing, by the ear-worn electronic device, a three-dimensional virtual sound environment comprising relaxing sounds;

generating, by the ear-worn electronic device, verbal instructions within the three-dimensional virtual sound environment that guide the wearer through a predetermined mental exercise that promotes wearer relaxation;

sensing, during the predetermined mental exercise, at least one physiologic parameter from the wearer by the ear-worn electronic device;

sensing, during the predetermined mental exercise, movement of the wearer by the ear-worn electronic device; and generating, by the ear-worn electronic device, verbal commentary that assesses wearer compliance with the predetermined mental exercise in response to one or both of the at least one physiologic parameter and the sensed movement of the wearer.

Item 2 is the method of item 1, comprising evaluating an effectiveness of the mental exercise in response to the at least one physiologic parameter.

Item 3 is the method of item 1, wherein the at least one physiologic parameter comprises a parameter indicative of the wearer's mental state.

Item 4 is the method of item 1, wherein the at least one physiologic parameter comprises an electroencephalogram (EEG) signal and one or both of a parameter indicative of heart rate and a parameter indicative of breathing.

Item 5 is the method of item 1, wherein:

the at least one physiologic parameter comprises an electroencephalogram (EEG) signal and a parameter indicative of breathing; and the method further comprises using an association between the EEG signal and the breathing parameter to determine the wearer's focus on breathing during the mental exercise.

Item 6 is the method of item 1, further comprising:

detecting noncompliance with the predetermined mental exercise by the wearer in response to a deviation in one or both of the sensed movement of the wearer and the at least one physiologic parameter;

wherein generating the verbal commentary comprises generating verbal commentary that encourages wearer compliance with the predetermined mental exercise.

Item 7 is the method of item 6, wherein the deviation is indicative of wearer distraction or an increase in wearer stress.

Item 8 is the method of item 1, further comprising modifying the verbal instructions that guide the wearer through the predetermined mental exercise in response to a level of wearer expertise in performing the predetermined mental exercise.

Item 9 is the method of item 1, further comprising:

classifying a sound of interest received by the ear-worn electronic device during the mental exercise; and performing one or both of:

generating verbal commentary suggesting that the wearer either ignore or consider the sound of interest in response to the classification of the sound of interest; and selectively implementing noise cancellation to either cancel or pass the sound of interest based on the classification of the sound of interest.

Item 10 is the method of item 1, further comprising maintaining realism of the three-dimensional virtual sound environment in response to sensing movement of the wearer during performance of the predetermined mental exercise.

Item 11 is the method of item 1, comprising:

collecting data generated during the predetermined mental exercise to produce a user profile for the wearer;

performing the method by a plurality of wearers of the ear-worn electronic devices;

collecting data generated by the ear-worn electronic devices of the plurality of wearers to produce a population profile; and updating the wearer's user profile using data from the population profile.

Item 12 is an ear-worn electronic device configured to be worn by a wearer and comprising:

a right ear device comprising a first processor;

a left ear device comprising a second processor communicatively coupled to the first processor;

a physiologic sensor module comprising one or more physiologic sensors configured to sense at least one physiologic parameter from the wearer;

a motion sensor module comprising one or more sensors configured to sense movement of the wearer;

the first and second processors coupled to the physiologic and motion sensor modules; and the first and second processors configured to produce a three-dimensional virtual sound environment comprising relaxing sounds, generate verbal instructions within the three-dimensional virtual sound environment that guide the wearer through a predetermined mental exercise that promotes wearer relaxation, and generate verbal commentary that assesses wearer compliance with the predetermined mental exercise in response to one or both of the sensed movement and the at least one physiologic parameter.

Item 13 is the device of item 12, wherein at least one of the first and second processors is configured to evaluate an effectiveness of the mental exercise in response to the at least one physiologic parameter.

Item 14 is the device of item 12, wherein the at least one physiologic parameter comprises a parameter indicative of the wearer's mental state.

Item 15 is the device of item 12, wherein the at least one physiologic parameter comprises an electroencephalogram (EEG) signal and one or both of a parameter indicative of heart rate and a parameter indicative of breathing.

Item 16 is the device of item 12, wherein:

the at least one physiologic parameter comprises an electroencephalogram (EEG) signal and a parameter indicative of breathing; and at least one of the first and second processors is configured to use an association between the EEG signal and the breathing parameter to determine the wearer's focus on breathing during the mental exercise.

Item 17 is the device of item 12, wherein:

at least one of the first and second processors is configured to detect noncompliance with the predetermined mental exercise by the wearer in response to detecting a deviation in one or both of the sensed movement of the wearer and the at least one physiologic parameter; and the first and second processors are configured to generate verbal commentary that encourages wearer compliance with the predetermined mental exercise.

Item 18 is the device of item 17, wherein the deviation is indicative of wearer distraction or an increase in wearer stress.

Item 19 is the device of item 12, wherein the first and second processors are configured to modify the verbal instructions that guide the wearer through the predetermined mental exercise in response to a level of wearer expertise in performing the predetermined mental exercise.

Item 20 is the device of item 12, wherein:

at least one of the first and second processors is configured to classify a sound of interest received by the ear-worn electronic device during the mental exercise; and the first and second processors are configured to:

generate verbal commentary suggesting that the wearer either ignore or consider the sound of interest in response to the classification of the sound of interest; and selectively implement noise cancellation to either cancel or pass the sound of interest based on the classification of the sound of interest.

Item 21 is the device of item 12, wherein the first and second processors are configured to maintain realism of the three-dimensional virtual sound environment in response to sensing movement of the wearer during performance of the predetermined mental exercise.

Item 22 is the device of item 12, wherein:
at least one of the first and second processors is configured to collect data generated during the predetermined mental exercise to produce a user profile for the wearer and to communicate with a remote server via a gateway device; and
the remote server is configured to:
collect data generated by ear-worn electronic devices of a plurality of wearers to produce a population profile; and
update the wearer's user profile using data from the population profile.

Item 23 is the device of item 12, comprising a wireless transceiver configured to wirelessly communicate with one or more external sensors or wearable devices.

Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

What is claimed is:

1. A method implemented by a hearing device configured to be worn by a wearer, the method comprising:
producing, by the hearing device, a virtual sound environment comprising relaxing sounds;
generating, by the hearing device, verbal instructions that guide the wearer through a predetermined exercise that promotes wearer relaxation;
monitoring one or both of a mental state and a physical state of the wearer during the predetermined exercise; and
in response to the monitoring, producing an output responsive to one or both of the wearer's mental state and physical state.

2. The method of claim 1, wherein:
monitoring comprising monitoring the mental state and the physical state of the wearer during the predetermined exercise; and
producing comprises producing the output responsive to the wearer's mental state and physical state.

3. The method of claim 1, wherein the predetermined exercise comprises a predetermined mental exercise involving a predetermined pattern of physical movement.

4. The method of claim 1, wherein the predetermined exercise comprises one of yoga, Tai Chi, and Qi Gong.

5. The method of claim 1, wherein the predetermined exercise comprises a predetermined mental exercise involving one of meditation, mindfulness, and hypnosis.

6. The method of claim 1, wherein monitoring comprises monitoring one or both of:
a physiologic response of the wearer to performing the predetermined exercise; and
three-dimensional movement of the wearer while performing the predetermined exercise.

7. The method of claim 1, wherein monitoring comprises monitoring one or more of blood oxygen saturation, body temperature, and heart rate.

8. The method of claim 1, wherein monitoring comprises monitoring stress of the wearer during the predetermined exercise in response to sensing one or more of blood oxygen saturation, body temperature, and heart rate.

9. The method of claim 1, wherein producing the output comprises generating, by the hearing device, verbal commentary that assesses wearer compliance with the predetermined exercise in response to monitoring one or both of the mental state and the physical state of the wearer during the predetermined exercise.

10. The method of claim 1, wherein producing the output comprises:
producing a user profile for the wearer using information relating to one or both of the implementation and execution of the predetermined exercise; and
updating the wearer's user profile over time using the information produced during subsequent iterations of the predetermined exercise by the wearer.

11. The method of claim 1, wherein the hearing device comprises a right-ear hearing device communicatively coupled to a left-ear hearing device.

12. The method of claim 1, wherein the relaxing sounds comprise binaural beats.

13. A hearing device configured to be worn by a wearer and comprising:
a processor operatively coupled to an audio output device and configured to produce a virtual sound environment comprising relaxing sounds and to generate verbal instructions that guide the wearer through a predetermined exercise that promotes wearer relaxation; and
a sensor module coupled to the processor and configured to monitor one or both of a mental state and a physical state of the wearer during the predetermined exercise;
wherein the processor is configured to produce an output responsive to one or both of the wearer's mental state and physical state using monitoring data generated by the sensor module.

14. The device of claim 13, wherein:
the sensor module is configured to monitor the mental state and the physical state of the wearer during the predetermined exercise; and
the processor is configured to produce an output responsive to the wearer's mental state and physical state in response to monitoring data generated by the sensor module.

15. The device of claim 13, wherein the predetermined exercise comprises a predetermined mental exercise involving a predetermined pattern of physical movement.

16. The device of claim 13, wherein the predetermined exercise comprises one of yoga, Tai Chi, and Qi Gong.

17. The device of claim 13, wherein the predetermined exercise comprises a predetermined mental exercise involving one of meditation, mindfulness, and hypnosis.

18. The device claim 13, wherein the sensor module is configured to monitor one or both of:
a physiologic response of the wearer to performing the predetermined exercise; and
three-dimensional movement of the wearer while performing the predetermined exercise.

19. The device of claim 13, wherein the sensor module comprises one or more physiologic sensors configured to sense one or more of blood oxygen saturation, body temperature, and heart rate.

20. The device of claim 13, wherein:
the sensor module comprises one or more physiologic sensors configured to sense one or more of blood oxygen saturation, body temperature, and heart rate; and the sensor module is configured to monitor stress of the wearer during the predetermined exercise in response to one or more of blood oxygen saturation, body temperature, and heart rate sensed by the one or more physiologic sensors.

21. The device of claim 13, wherein the processor and the audio output device are configured to generate verbal commentary that assesses wearer compliance with the predetermined exercise in response to monitoring one or both of the mental state and the physical state of the wearer during the predetermined exercise by the sensor module.

22. The device of claim 13, wherein the processor or a processor remote from the device is configured to:
    produce a user profile for the wearer using information relating to one or both of the implementation and execution of the predetermined exercise; and
    update the wearer's user profile over time using the information produced during subsequent iterations of the predetermined exercise by the wearer.

23. The device of claim 13, wherein the hearing device comprises a right-ear hearing device communicatively coupled to a left-ear hearing device.

24. The device of claim 13, wherein the relaxing sounds comprise binaural beats.

25. A hearing device configured to be worn by a wearer and comprising:
    a processor operatively coupled to an audio output device and configured to produce a virtual sound environment comprising relaxing sounds and to generate verbal instructions that guide the wearer through a predetermined exercise that promotes wearer relaxation; and
    a sensor module coupled to the processor and comprising one or more physiologic sensors configured to sense one or more of blood oxygen saturation, body temperature, and heart rate, the sensor module configured to monitor one or both of a mental state and a physical state of the wearer during the predetermined exercise using the one or more physiologic sensors, wherein:
        the processor is configured to produce an output responsive to one or both of the wearer's mental state and physical state using monitoring data generated by the sensor module; and
        the processor and the audio output device are configured to generate verbal commentary that assesses wearer compliance with the predetermined exercise in response to monitoring one or both of the mental state and the physical state of the wearer during the predetermined exercise by the sensor module.

* * * * *